US011389131B2

United States Patent
Tuzoff et al.

(10) Patent No.: US 11,389,131 B2
(45) Date of Patent: Jul. 19, 2022

(54) SYSTEMS AND METHODS FOR PROCESSING OF DENTAL IMAGES

(71) Applicant: DENTI.AI TECHNOLOGY INC., Toronto (CA)

(72) Inventors: Dmitry Tuzoff, Saint Petersburg (RU); Alexey Krasnov, Moscow (RU); Max Kharchenko, Moscow (RU); Lyudmila Tuzova, Saint Petersburg (RU)

(73) Assignee: Denti.Ai Technology Inc., Toronto (CA)

( * ) Notice: Subject to any disclaimer, the term of this patent is extended or adjusted under 35 U.S.C. 154(b) by 44 days.

(21) Appl. No.: 16/454,902

(22) Filed: Jun. 27, 2019

(65) Prior Publication Data

US 2020/0146646 A1 May 14, 2020

Related U.S. Application Data

(60) Provisional application No. 62/690,844, filed on Jun. 27, 2018.

(51) Int. Cl.
*G06K 9/00* (2022.01)
*A61B 6/00* (2006.01)
(Continued)

(52) U.S. Cl.
CPC .............. *A61B 6/5217* (2013.01); *A61B 6/14* (2013.01); *A61B 6/563* (2013.01); *G06T 7/0012* (2013.01);
(Continued)

(58) Field of Classification Search
CPC . A61B 6/14; A61B 6/145; G06T 2207/30036; G06T 2207/2008; G06T 2207/20084
See application file for complete search history.

(56) References Cited

U.S. PATENT DOCUMENTS 5,839,438 A 11/1998 Grattinger et al.
6,209,095 B1 3/2001 Anderson et al.
(Continued)

FOREIGN PATENT DOCUMENTS

CN 102598054 A 7/2012
CN 108389207 A 8/2018
(Continued)

OTHER PUBLICATIONS

Doi K. Computer-aided diagnosis in medical imaging: Historical review, current status and future potential. Comput Med Imaging Graph. 2007; 31(4-5): p. 198-211.
(Continued)

*Primary Examiner* — Atiba O Fitzpatrick
(74) *Attorney, Agent, or Firm* — Jenna L. R. Wilson; Wilson Lue LLP

(57) ABSTRACT

A computer system implements a neural network to process raw dental images to detect and number teeth and to diagnose pathological, non-pathological, and post-treatment conditions. Detected teeth, corresponding numbers, and any corresponding detected conditions are correlated to the dental image and presented in a graphical user interface comprising the image and a standard, symbolic dental chart associating the tooth number, detected conditions, and regions of the image to teeth represented in the symbolic chart.

32 Claims, 9 Drawing Sheets

(51) Int. Cl.
  *G06T 7/00*  (2017.01)
  *A61B 6/14*  (2006.01)
(52) U.S. Cl.
  CPC .................. *G06T 2200/24* (2013.01); *G06T 2207/20084* (2013.01); *G06T 2207/30036* (2013.01)

(56) References Cited

U.S. PATENT DOCUMENTS

| | | | |
|---|---|---|---|
| 6,409,504 B1 | 6/2002 | Jones et al. | |
| 6,532,299 B1 | 3/2003 | Sachdeva et al. | |
| 6,736,776 B2 | 5/2004 | Miles | |
| 7,010,153 B2 | 3/2006 | Zimmermann | |
| 7,263,492 B1 | 8/2007 | Suresh et al. | |
| 7,269,278 B2 | 9/2007 | Cong et al. | |
| 7,391,895 B2 | 6/2008 | Wang et al. | |
| 7,421,398 B2 | 9/2008 | Kimmel | |
| 7,472,275 B2 | 12/2008 | Arnouse | |
| 7,596,253 B2 | 9/2009 | Wong et al. | |
| 7,602,965 B2 | 10/2009 | Hong et al. | |
| 7,822,621 B1 | 10/2010 | Chappel | |
| 8,416,984 B2 | 4/2013 | Liang et al. | |
| 8,417,010 B1 | 4/2013 | Colby | |
| 8,463,716 B2 | 6/2013 | Montgomery et al. | |
| 8,687,859 B2 | 4/2014 | Yan et al. | |
| 8,737,706 B2 | 5/2014 | Graham et al. | |
| 8,761,493 B2 | 6/2014 | Chen et al. | |
| 8,768,016 B2 | 7/2014 | Pan et al. | |
| 8,929,635 B2 | 1/2015 | Chen et al. | |
| 9,020,236 B2 | 4/2015 | Wang et al. | |
| 9,158,889 B2 | 10/2015 | Badawi | |
| 9,339,245 B2 | 5/2016 | Colby | |
| 9,477,649 B1 | 10/2016 | Davidson et al. | |
| 9,710,603 B2* | 7/2017 | Kaminski | A61C 19/00 |
| 9,839,402 B2 | 12/2017 | Colby | |
| 9,886,178 B2 | 2/2018 | Kendall et al. | |
| 10,043,073 B2 | 8/2018 | Ross et al. | |
| 10,049,457 B2 | 9/2018 | Abraham et al. | |
| 10,201,318 B2 | 2/2019 | Tsuji et al. | |
| 10,410,363 B2 | 9/2019 | Dekel et al. | |
| 10,426,351 B2 | 10/2019 | Abrams et al. | |
| 10,722,191 B2 | 7/2020 | Colby | |
| 2002/0178032 A1* | 11/2002 | Benn | G16H 40/63 705/2 |
| 2004/0038184 A1 | 2/2004 | Adachi et al. | |
| 2005/0203777 A1 | 9/2005 | Rosenfeld et al. | |
| 2006/0069591 A1 | 3/2006 | Razzano | |
| 2006/0147872 A1 | 7/2006 | Andreiko | |
| 2006/0173985 A1 | 7/2006 | Moore | |
| 2007/0217648 A1 | 9/2007 | Muehlbauer | |
| 2007/0294104 A1 | 12/2007 | Boaz et al. | |
| 2009/0076960 A2 | 3/2009 | Hamel et al. | |
| 2011/0119088 A1 | 5/2011 | Gunn | |
| 2011/0153351 A1 | 6/2011 | Vesper et al. | |
| 2012/0148986 A1 | 6/2012 | Yan et al. | |
| 2013/0022251 A1 | 1/2013 | Chen et al. | |
| 2013/0122468 A1* | 5/2013 | Abrams | A61B 6/5217 433/215 |
| 2013/0243276 A1 | 9/2013 | Souza et al. | |
| 2014/0142984 A1 | 5/2014 | Wright et al. | |
| 2014/0149128 A1 | 5/2014 | Getchius | |
| 2014/0278529 A1 | 9/2014 | Matos | |
| 2014/0314288 A1 | 10/2014 | Roychowdhury et al. | |
| 2014/0342301 A1 | 11/2014 | Fleer et al. | |
| 2014/0379361 A1 | 12/2014 | Mahadkar et al. | |
| 2015/0046181 A1 | 2/2015 | Adjaoute | |
| 2015/0237106 A1 | 8/2015 | Golay | |
| 2016/0004811 A1 | 1/2016 | Somasundaram et al. | |
| 2016/0014288 A1 | 1/2016 | Ono | |
| 2016/0038092 A1 | 2/2016 | Golay | |
| 2016/0196389 A1 | 7/2016 | Moturu et al. | |
| 2017/0053562 A1 | 2/2017 | Bova et al. | |
| 2017/0083672 A1 | 3/2017 | Juneau et al. | |
| 2017/0161439 A1 | 6/2017 | Raduchel et al. | |
| 2018/0033009 A1 | 2/2018 | Goldman et al. | |
| 2018/0235437 A1 | 3/2018 | Ozerov et al. | |
| 2018/0122509 A1 | 5/2018 | Christiansson | |
| 2018/0174367 A1 | 6/2018 | Marom | |
| 2018/0182039 A1 | 6/2018 | Wang et al. | |
| 2018/0206940 A1 | 7/2018 | Kopelan et al. | |
| 2018/0366225 A1 | 12/2018 | Mansi et al. | |
| 2019/0026598 A1* | 1/2019 | Salah | G06K 9/6201 |
| 2019/0038367 A1* | 2/2019 | Ciriello | A61B 34/00 |
| 2019/0043607 A1* | 2/2019 | Sears | G16H 30/20 |
| 2019/0065685 A1* | 2/2019 | Pickover | G06F 21/64 |
| 2019/0066835 A1 | 2/2019 | Lyman et al. | |
| 2019/0110753 A1 | 4/2019 | Zhang et al. | |
| 2019/0130566 A1 | 5/2019 | Niemeijer et al. | |
| 2019/0175314 A1* | 6/2019 | Lagardere | A61C 9/0053 |
| 2019/0313963 A1* | 10/2019 | Hillen | G06N 3/0454 |
| 2019/0333627 A1* | 10/2019 | Johnson | G06N 3/0454 |
| 2020/0015943 A1* | 1/2020 | Reynard | G16H 40/63 |
| 2020/0134823 A1 | 4/2020 | Emoto et al. | |
| 2020/0138518 A1 | 5/2020 | Lang | |
| 2020/0305808 A1 | 10/2020 | Ezhov et al. | |
| 2020/0320685 A1* | 10/2020 | Anssari Moin | G06T 11/008 |
| 2020/0381105 A1 | 12/2020 | Bernard et al. | |
| 2021/0082184 A1 | 3/2021 | Claessen et al. | |
| 2021/0192726 A1* | 6/2021 | Bergman | A61B 6/14 |

FOREIGN PATENT DOCUMENTS

| | | |
|---|---|---|
| CN | 108463172 A | 8/2018 |
| CN | 208172859 U | 11/2018 |
| JP | 2005050246 A1 | 2/2005 |
| KR | 20050020139 A | 3/2005 |
| WO | 2017093563 A1 | 6/2017 |
| WO | 2018033762 A1 | 2/2018 |

OTHER PUBLICATIONS

Rezaei M, Yang H, Meinel C. Deep Neural Network with l2-norm Unit for Brain Lesions Detection. In International Conference on Neural Information Processing; 2017. p. 798-807.

Lin PL, Lai YH, Huang PW. An effective classification and numbering system for dental bitewing radiographs using teeth region and contour information. Pattern Recognit. 2010; 43(4): p. 1380-1392.

Hosntalab M, Zoroofi RA, Tehrani-Fard AA, Shirani G. Classification and numbering of teeth in multi-slice CT images using wavelet-Fourier descriptor. Int J Comput Assist Radiol Surg. 2010; 5(3): p. 237-249.

Miki Y, Muramatsu C, Hayashi T, Zhou X, Hara T, Katsumata A, et al. Classification of teeth in cone-beam CT using deep convolutional neural network. Comput Biol Med. 2016; 80: p. 24-29.

Krizhevsky A, Sutskever I, Hinton GE. ImageNet classification with deep convolutional neural networks. In Annual Conference on Neural Information Processing Systems (NIPS); 2012. p. 1097-1105.

LeCun Y, Bottou L, Bengio Y, Haffner P. Gradient-based learning applied to document recognition. Proc IEEE. 1998; 86(11): p. 2278-2323.

Huang J, Rathod V, Sun C, Zhu M, Korattikara A, Fathi A, et al. Speed/Accuracy Trade-Offs for Modern Convolutional Object Detectors. In The IEEE Conference on Computer Vision and Pattern Recognition (CVPR); Jul. 2017 p. 3296-3297.

LeCun Y, Bengio Y, Hinton G. Deep learning. Nature. 2015; 521: p. 436-444.

Lee H, Park M, Kim J. Cephalometric Landmark Detection in Dental X-ray Images Using Convolutional Neural Networks. In SPIE Medical Imaging; 2017. p. 1-6.

Ö. Arik S, Ibragimov B, Xing L. Fully automated quantitative cephalometry using convolutional neural networks. J Med Imaging. 2017; 4(1): p. 014501-014501.

Wang CW, Huang CT, Lee JH, Li CH, Chang SW, Siao MJ, et al. A benchmark for comparison of dental radiography analysis algorithms. Med Image Anal. 2016; 31: p. 63-76.

Liu J, Wang D, Lu L, Wei Z, Kim L, Turkbey EB, et al. Detection and diagnosis of colitis on computed tomography using deep convolutional neural networks. Med Phys. 2017; 44(9): p. 4630-4642.

(56) References Cited

OTHER PUBLICATIONS

Ren S, He K, Girshick R, Sun J. Faster R-CNN: Towards Real-Time Object Detection with Region Proposal Networks. IEEE Trans Pattern Anal Mach Intell. 2017; 39: p. 1137-1149.

Simonyan K, Zisserman A. Very Deep Convolutional Networks for Large-Scale Image Recognition. In International Conference on Learning Representations (ICLR); May 2015.

Deng J, Dong W, Socher R, Li LJ, Li K, Fei-Fei L. ImageNet: A large-scale hierarchical image database. In The Conference on Computer Vision and Pattern Recognition (CVPR); 2009. p. 248-255.

Abadi M, Agarwal A, Barham P, Brevdo E, Chen Z, Citro C, et al. TensorFlow: Large-Scale Machine Learning on Heterogeneous Systems. 2015. Available from: tensorflow.org.

Jung A. Image augmentation for machine learning experiments. 2015. Available from: https://imgaug.readthedocs.io/en/latest/. Accessed Nov. 29, 2019, 1 pg.

Ahmed, Musheer, "Augmenting Accountability, Security And Fraud Detection In Health Data Sharing Systems", Georgia Institute Of Technology, May 2016, 148 pgs.

Harris, John B., "8 Rules For E-Signature Security", SIGNiX, 2014, 48 pgs.

Reducing Healthcare Fraud In Africa; Genkey Solutions b.v., 2016, 12 pgs.

Tian Sukun et al: "Automatic Classification and Segmentation of Teeth on 3D Dental Model Using Hierarchical Deep Learning Networks", IEEE Access, vol. 7, Jun. 21, 2019. pp. 84817-84828, XP011734278, 001:10.1109/ACCESS.2019.2924262 [retrieved on Jul. 9, 2019].

Fracaro et al., "The Sensitivity and specificity of Clinical Assessment Compared with Bitewing Radiology for Detection of Occlusal Dentin Caries", American Academy of Pediatric Dentistry 23:3, Mar. 22, 2001, pp. 204-210.

Markowitz et al. "In Vitro Study of the Diagnostic Performance of the Spectra Caries Detention Aid", The Journal of Clinical Dentistry, 2015,17-22,vol. XXXVI No. 1., 6 pgs.

Lee et al. "Diagnosis And Prediction Of Periodontally Compromised Teeth Using a Deep Learning-Based Convolutional Neural Network Algorithm", Journal of Periodontal & Implant Science, Apr. 23, 2018, pp. 114-123.

Lee et al., "Detection And Diagnosis Of Dental Caries Using Deep Learning-Based Convolutional Neural Network Algorithm", Journal of Dentistry, Jul. 25, 2018, 106-111, 77, 6 pgs.

Hwang et al. "An Overview of Deep Learning in the Field of Dentistry", Image Science in Dentistry, Mar. 25, 2019, 49: 1-7.

Murata et al., "Towards a Fully Automated Diagnostic System for Orthodontic Treatment in Dentistry," IEEE Computer Society, 2017, pp. 1-8, 131h international conference on eScience.

Shankeeth et al.,"Automated detection of third molars and mandibular nerve by deep learning" (pp. 1-7), Jun. 21, 2019.

S. B. Kotsiantis, "Supervised Machine Learning: A Review of Classification Techniques", Jul. 16, 2007, Informatica 31 (2007) pp. 249-268.

L. C. Rabelo, A. Jones and Y. Yih, "Development of a real-time learning scheduler using reinforcement learning concepts," 1994, 7 pgs.

R. Ho, "Pragmatic Programming Techniques: Characteristics of Machine Learning Model", Feb. 19, 2012, BlogSpot, 3 pgs.

Azmi et al., "Freeman Chain Code Representation in Signature Fraud Detection Based on Nearest Neighbor and ANN Classifiers", International Journal of Image Processing (IJIP), vol. 8 : Issue (6) : 2014, pp. 434-454.

Calberson et al., "Fraudulent Use of Digital Radiography: Methods to Detect and Protect Digital Radiographs", 2008, JOE, 34(5), pp. 530-536.

Young-Jun Yu: "Machine Learning for Dental Image Analysis", Nov. 29, 2016, Retrieved from https://arxiv.org/ftp/arxiv/papers/1611/1611.09958.pdf, 24 pgs.

* cited by examiner

SYSTEMS AND METHODS FOR PROCESSING OF DENTAL IMAGES

CROSS-REFERENCE TO RELATED APPLICATIONS

This application claims priority to U.S. Provisional Application No. 62/690,844 filed on Jun. 27, 2018, the entirety of which is incorporated herein by reference.

TECHNICAL FIELD

The present disclosure relates to image processing and, in particular, to processing of dental imaging and conversion of the raw image data and diagnostic findings into the symbolic representations corresponding to the international standards in dentistry.

TECHNICAL BACKGROUND

Analysis of dental imaging, such as radiographs, and recording the results of such analysis in the form of dental charts is an important element of daily clinical practice. Radiographs such as panoramic radiographs, bitewings, Full-Mouth Series (FMX), and Cone-Beam Computer Tomographs (CBCT), provide images of more than one of a patient's teeth. When a dental image includes more than one tooth, one of the tasks of a human expert analyzing the image is to perform teeth detection and numbering. This is preferably done according to a recognized notation, such as the FDI notation published by the International Organization for Standardization (e.g., ISO 3950:2016). Accurate analysis of dental imaging is a precursor to the detection of pathologies and to the general management of the majority of dental practices. However, the routine nature of dental charting diverts significant time and attention in dental practice.

Computer-aided diagnosis (CAD) has developed significantly due to the growing accessibility of digital medical data, rising computational power and progress in artificial intelligence. CAD systems assisting physicians and radiologists in decision-making have been applied to various medical problems, such as breast and colon cancer detection, classification of lung diseases, and localization of brain lesions.

Despite existing approaches, barriers remain to the reliable automation of dental imaging analysis.

BRIEF DESCRIPTION OF THE DRAWINGS

In drawings which illustrate by way of example only embodiments of the present application.

DETAILED DESCRIPTION

The examples and embodiments described in this disclosure provide systems, methods, and data processing device-readable media for processing dental imaging. In particular, the example system and methods described herein apply deep learning techniques to the processing of dental images to provide a platform for computer-aided diagnosis and charting, and in particular to detect and number teeth. Deep learning is a class of learnable artificial intelligence (AI) algorithms that allows a computer program to automatically extract and learn important features of input data for further interpretation of previously unseen samples. Deep learning techniques differ from conventional image processing techniques in that deep learning techniques can learn from a raw data input, for example pixels of images, with no hand-crafted feature engineering required. A detailed overview of deep learning techniques is available in LeCun Y, Bengio Y, Hinton G, "Deep Learning", Nature, 2015; 521: p. 436-444.

Figure 1:
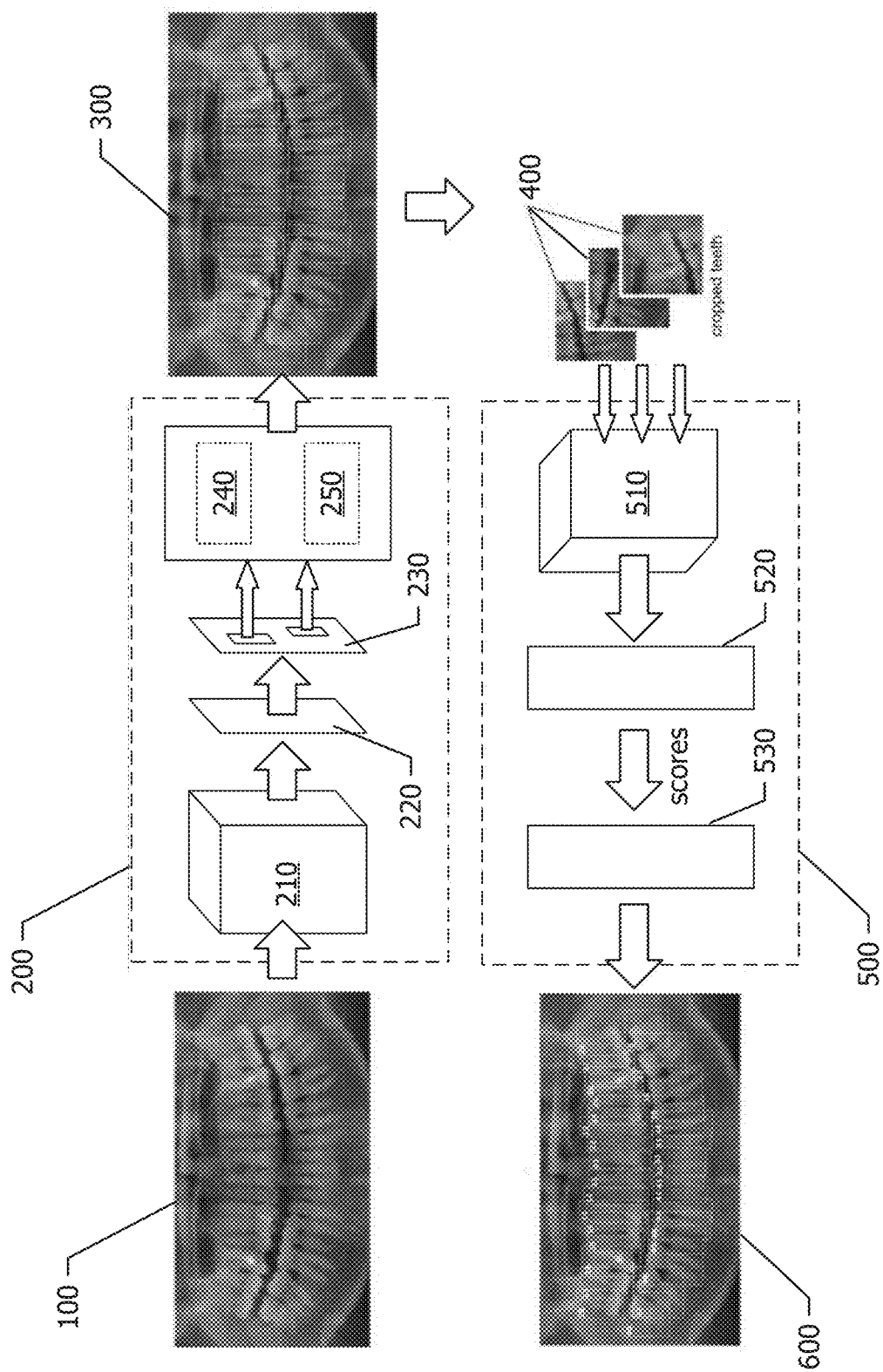
FIG. 1 is a schematic illustration of a workflow and select system components of a system for processing dental imaging.

An example workflow for detecting and numbering teeth using deep learning is illustrated schematically in FIG. 1. In this example, a system implementing deep learning techniques includes a detection module and a classification or numbering module, both applying deep learning techniques to detect and classify teeth, respectively, in a source dental image. The detection module receives the source dental image and generates data identifying image regions determined to correspond to individual teeth. The identifying data can take the form of bounding boxes defining a boundary for each tooth captured in the dental image. Output from the detection module is then provided to the classification module to assign a number to each detected tooth. Numbering may be assigned in accordance with the FDI notation, the Universal Numbering System, the Palmer notation method, or any other suitable dental notation. In the accompanying figures, either FDI notation or the Universal Numbering System is employed.

In one embodiment, convolutional neural networks (CNNs) are utilized for both detection and numbering of teeth. CNNs are a standard class of architectures for deep feedforward neural networks, and they are applicable for image recognition tasks (see e.g., LeCun Y, Bottou L, Bengio Y, Haffner P. Gradient-based learning applied to document recognition. Proc IEEE. 1998; 86 (11): p. 2278-2323). CNN architectures exploit specific characteristics of an image data input, such as spatial relationships between objects, to effectively represent and learn hierarchical features using multiple levels of abstraction. Those skilled in the art will recognize, however, that appropriate neural network models based on architectures other than CNNs may be employed.

In the example of FIG. 1, the source image 100 is provided in a digital format as input to the detection module 200. If the source image is initially produced on film, the image is initially digitized. In the examples discussed herein, source images are panoramic view (PV) radiographs that depict the upper and lower jaws in one single image.

However, those skilled in the art will appreciate that these examples need not be limited to PV radiographs. Other types of dental images, such as medical computed tomography scans and bitewing radiographs, intraoral three-dimensional scans, still images and videos may be employed as input. PV and bitewing intraoral radiographs in particular are convenient because they permit screening of a broad anatomical region while requiring relatively low radiation doses, and are in relatively common usage.

The detection module detects teeth in the original image. Teeth detection may comprise implementation of the Faster R-CNN model disclosed in Ren S, He K, Girshick R, Sun J. Faster R-CNN: Towards Real-Time Object Detection with Region Proposal Networks. IEEE Trans Pattern Anal Mach Intell. 2017; 39: p. 1137-1149. Faster R-CNN is a single unified network consisting of two modules: the regional proposal network (RPN) and object detector. The RPN module proposes regions where objects of interest might be located. The object detection module uses these proposals for further object localization and classification. Both the RPN and object detector modules share the convolution layers 210 of the base CNN that provides a compact representation of the source image, known as a feature map 220. The features are learned during a training phase, unlike in classical computer vision techniques in which features are engineered by hand.

To generate regional proposals, the RPN module slides a window over the feature map 220, and, at each window location, produces potential bounding boxes named "anchors". For each anchor, the RPN module estimates the probability that the anchor contains an object or a background (e.g., employing a softmax function), and tightens the bounding box with a specialized bounding box regressor to identify region proposals. The top N-ranked region proposals (indicated schematically in 230) then serve as input for the object detection module. One head 240 of the object detection module carries out a binary (two-class) detection task on each region of interest thus identified, refining the determination whether the region of interest is a tooth or a background. Another head 250 of the object detection module generates the final bounding box coordinates, represented schematically on the original input image as outlines in image 300.

A VGG-16 Net (Simonyan K, Zisserman A. Very Deep Convolutional Networks for Large-Scale Image Recognition. In International Conference on Learning Representations (ICLR); 2015 May) can be used as a base CNN for both RPN and object detection. The hyperparameters that define the anchor properties are preferably tuned to reflect the potential boundaries of teeth. These hyperparameters include base anchor size, anchor scales, and anchor ratios.

Preferably, to minimize false positives during teeth detection, the Intersection-over-Union (IoU) threshold for a non-maximum suppression algorithm (NMS) is used in the system and prediction score threshold is also tuned.

The output 300 of the detection module is provided to the classification module 500. The classification module 500 is trained to predict the number of a tooth according to a notation. In the example of FIG. 1, FDI notation is used. The classification module 500 is modelled according to a CNN such as the VGG-16 convolutional architecture 510. To classify the teeth by numbers, the classification module initially crops the image based on the predicted bounding boxes to produce cropped images 400, which are provided as input to convolutional layers 510. The classification module 500 then performs a 32-class detection task, e.g. using a softmax function 520, producing probabilities that each cropped image represents each of the 32 permanent teeth. This results in a set of confidence scores over 32 classes for each bounding box identified by the detection module 200, which can be used to predict a tooth number according to the desired (standard) notation. It should be noted that in these examples, an adult dental chart is used, although a primary dental chart and appropriate notation may be employed for younger patients.

However, in a post-processing stage, the classification module 500 may then apply heuristics or other constraints to the sets of confidence scores to improve prediction results. For example, a heuristic may comprise the assumption that each tooth can occur at most once in the image in a specific order, to ensure arrangement consistency among the detected teeth. In the case of bitewing images and intraoral scans, the input data to the classification module may also include information about the position of the sensor (in the case of an image or scan generated digitally) or the film, which imposes constraints on the teeth that are likely to appear in a given image.

In one embodiment, this post-processing comprises the following steps:

1. Sort predicted teeth bounding boxes by coordinates within each jaw.
2. Count the number of missed teeth based on the known maximum teeth count.
3. Iterate over all possible valid combinations of teeth and calculate the total confidence score.
4. Choose the combination with the highest total confidence score.

The system produces as output (6) the coordinates of the bounding boxes for the teeth detected in the source dental image, and corresponding teeth numbers for all detected teeth in the image.

Example

A system implementing the foregoing methodology was used to process a data set of 1574 anonymized PV radiographs of adults randomly chosen from the X-ray images archive provided by the Reutov Stomatological Clinic in Russia from January 2016 to March 2017. No additional information such as gender, age, or time of image taking was used. All PV images were captured with the Sirona Orthophos XG-3 X-ray unit (Sirona Dental Systems, GmbH, Bensheim, Germany). Five radiology experts of varying experience provided ground truth annotations for the images. To collect these annotations, the experts were presented with high-resolution PV images and asked to draw bounding boxes around all teeth and, at the same time, to provide a class label for each box with the tooth number (according to the FDI system).

The images were randomly distributed into a training group of 1352 images and a testing group of 222 images. The training group was used to train the teeth detection and classification models, and the testing group was used for evaluation of the performance of the approach.

Training

During training for teeth detection, model weights pre-trained on the ImageNet dataset were used for the basic CNN (Deng J, Dong W, Socher R, Li L J, Li K, Fei-Fei L. ImageNet: A large-scale hierarchical image database. In The Conference on Computer Vision and Pattern Recognition (CVPR); 2009. p. 248-255). All layers of the CNN were fine-tuned since the dataset was sufficiently large and different from ImageNet. The initial learning rate was chosen as 0.001 with further exponential decay. The model was trained only to detect teeth with natural roots, excluding dental implants and fixed bridges.

The detection module 200 was implemented using a customized version of the Faster R-CNN python (Hosang J. Faster RCNN TF. 2016. Available from github.com/small-corgi/Faster-RCNN_TF) implementation with the TensorFlow backend Abadi M, Agarwal A, Barham P, Brevdo E, Chen Z, Citro C, et al. TensorFlow: Large-Scale Machine Learning on Heterogeneous Systems. 2015. Available from tensorflow.org). The hyperparameters that define the anchor properties were tuned to reflect the potential boundaries of teeth. To minimize the false positives rate of teeth detection, the Intersection-over-Union (IoU) threshold for non-maximum suppression algorithm (NMS) used in the system and prediction score threshold were also tuned.

The classification module 500 was written using the Keras library (Chollet F. Keras. 2015. Available from github.com/fchollet/keras) with the TensorFlow backend. As with teeth detection, for teeth classification the model weights pre-trained on the ImageNet dataset were used to initialize the CNN in the classification module. For training, cropped images were produced based on the ground truth annotations of full panoramic X-rays, and the cropping method was tuned to include neighbouring structures, which improved the prediction quality of the CNN because of additional context. The images were also augmented to increase the variety of the available dataset. A batch size of 64 was used to train the CNN.

Performance Analysis

The testing group of 222 images was used to evaluate the performance of the system, and to compare it to human experts. Each image was analysed independently by the system and an experienced radiologist. The testing dataset was not seen by the system during the training phase.

The annotations made by the system and the experts were compared to evaluate the performance. A detailed analysis of all cases where human and machine annotations were not in agreement was performed by another experienced expert in dentomaxillofacial radiology to review possible causes of incorrect image interpretation. In such cases, the verifying expert had the final say to determine the ground truth. In the cases where the system and the expert provided the same annotations, both were considered correct.

For the detection task, the human and machine annotations were deemed to agree if they intersected substantially. The remaining unmatched boxes were composed of two error types: false positive results, where redundant boxes were annotated, and false negative results, where existent teeth were missed. For the numbering task, human and machine annotations were deemed to agree if the class labels provided by experts and the system for the same bounding boxes were identical.

Based on the results for detection and numbering tasks, metrics were calculated to evaluate the performance of the system and the human. For teeth detection, the following metrics were used:

$$\text{precision} = \frac{TP}{TP+FP}$$

$$\text{sensitivity} = \frac{TP}{TP+FN}$$

where TP, FP, and FN are true positive, false positive, and false negative, respectively. Accuracy in teeth numbering was calculated as the ratio of correctly classified boxes to all boxes.

Teeth Detection

The above system implemented for teeth detection achieved a sensitivity of 0.9941 and a precision of 0.9945. The experts achieved a sensitivity of 0.9980 and a precision of 0.9998. The detailed data are presented in Table 1 below.

TABLE 1

|  | System | Expert |
| --- | --- | --- |
| True positives | 5023 | 5043 |
| False negatives | 30 | 10 |
| False positives | 28 | 1 |
| Precision | 0.9945 | 0.9998 |
| Sensitivity | 0.9941 | 0.9980 |

Figure 2:
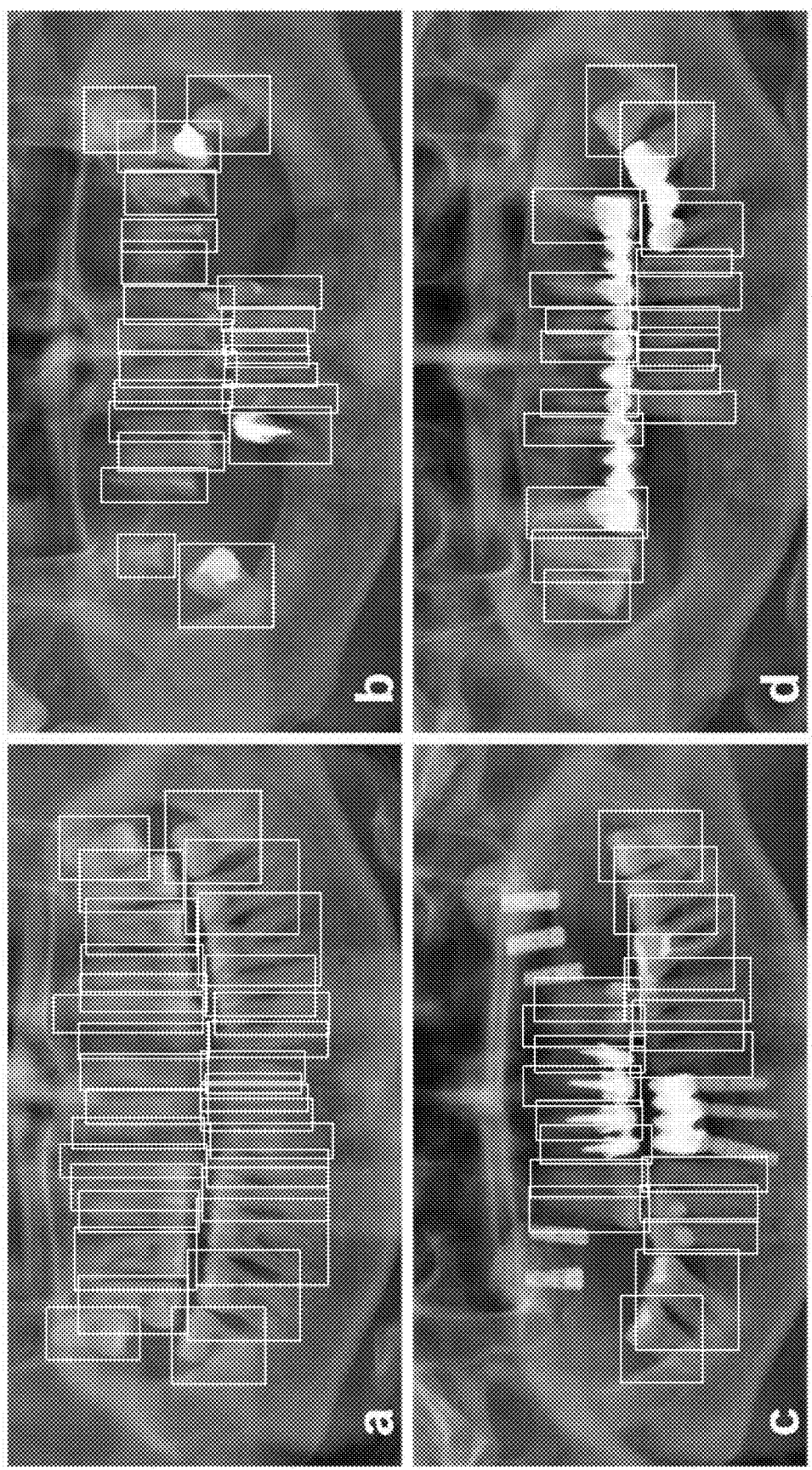
FIG. 2 is a set of images illustrating successful detection of teeth by the system of FIG. 1.

In general, the detection module 200 was found to demonstrate excellent results, both for high-quality images with normal teeth arrangement and more challenging cases such as overlapped or impacted teeth, images of a poor quality with blurred tooth contours, or teeth with crowns. It was found in the case of both teeth detection and numbering (classification) that errors made by the above-described system were due to similar factors giving rise to errors by the experts. FIG. 2 shows successful detection examples for (a) all 32 teeth, (b) severely decayed and impacted teeth, (c) exclusion of implants and detection of dental crowns, and (d) exclusion of cantilever elements of fixed bridges. The detected teeth are depicted with white boxes superimposed on the images.

In most cases, the detection module 200 correctly excluded bridges and implants from the detection results. The main reasons for faults included root remnants, presence of orthopaedic appliances, highly impacted and overlapped teeth. The system produced false positive results in the form of incorrectly detected implants and bridges, extra boxes for teeth with orthopaedic constructions and multiple-rooted teeth and detected fragments outside of the jaw. Most human errors were false negatives caused by missed root remnants, probably as a result of lack of concentration.

Teeth Numbering

The teeth classification by the classification module 500 achieved a sensitivity of 0.9800 and precision of 0.9994, while the experts achieved a sensitivity of 0.9893 and a precision of 0.9997. The detailed data are presented in Table 2 below. The Error statistics provide details on three groups of misdiagnosed teeth: 1 tooth distance (neighboring teeth were misclassified), >1 (the predicted number was more than 1 tooth apart from the correct number), confused jaws (upper and lower jaws were confused).

TABLE 2

|  | System | Expert |
| --- | --- | --- |
| True positives | 4938 | 4985 |
| True negatives | 156108 | 156155 |

TABLE 2-continued

|  | System | Expert |
|---|---|---|
| False negatives | 101 | 54 |
| False positives | 101 | 54 |
| Specificity | 0.9994 | 0.9997 |
| Sensitivity | 0.9800 | 0.9893 |

Figure 3:
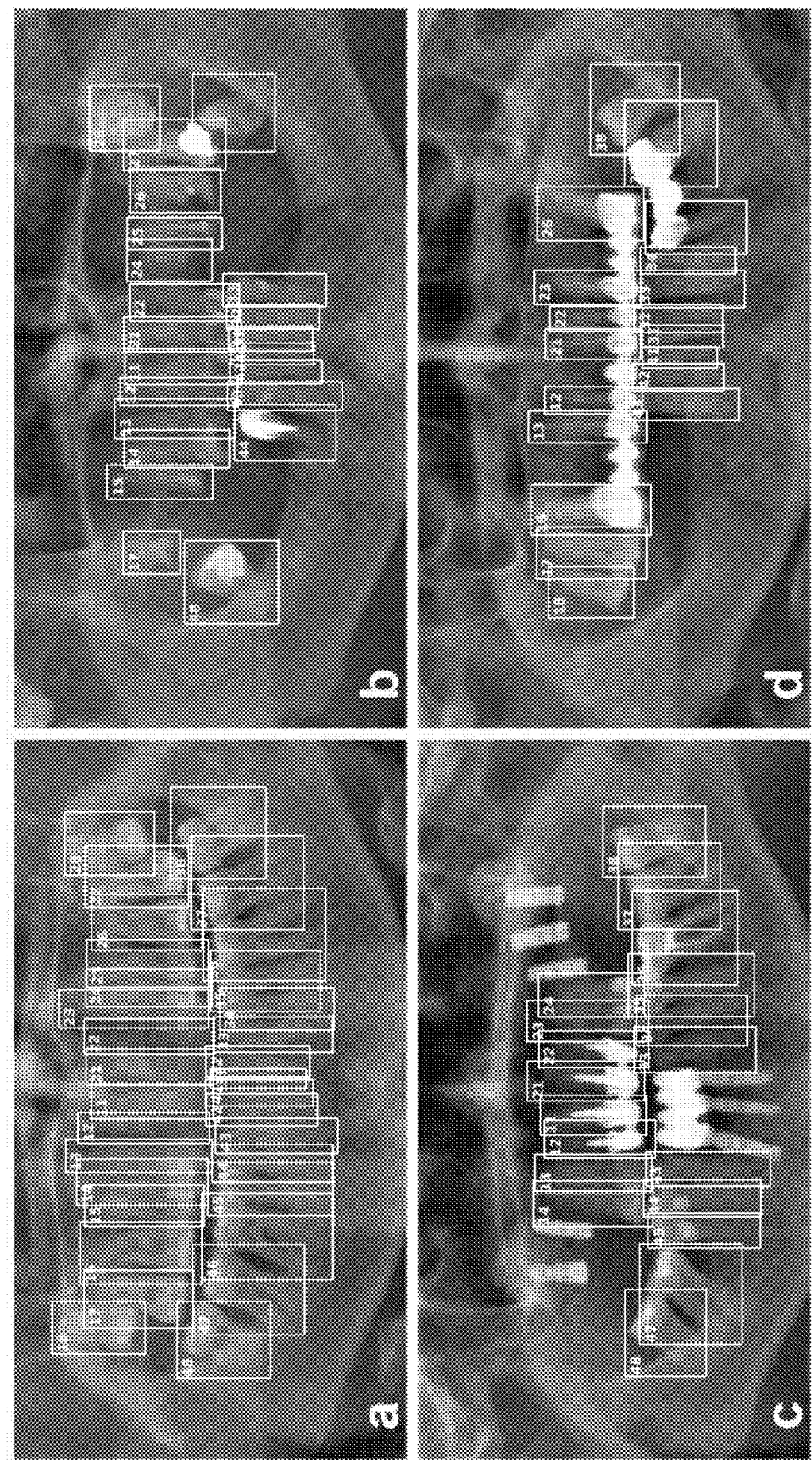
FIG. 3 is a set of images illustrating successful classification of teeth by the system of FIG. 1.

FIG. 3 shows successful classification examples for (a) all 32 teeth, (b) severely decayed and impacted teeth, (c) teeth with dental crowns, and (d) correct classification despite missed teeth and lack of context. Again, the detected teeth are indicated by white rectangles. The numbering in these examples conforms to FDI notation.

It was found that extending the region of cropped teeth to include additional context and augmenting the images resulted in approximately a 6 percentage point (pp) and a 2 pp increase of accuracy, respectively. The heuristic method based on spatial teeth number arrangement rules increased the accuracy by 0.5 pp.

The main reasons for numbering errors by the classification module 500 includes lack of nearby teeth near the target tooth, too small remaining tooth fragments (root remnants or severely decayed teeth), and evidence of extensive dental work. In most errors, the system confused a tooth with a missing adjacent one. Mainly, molars were misclassified. The same cases are reported by human experts to be challenging.

The foregoing results compare favourably to other studies, including Lin P L, Lai Y H, Huang P W, "An effective classification and numbering system for dental bitewing radiographs using teeth region and contour information", Pattern Recognit. 2010 43 (4) pp. 1380-1392; Hosntalab M, Zoroofi R A, Tehrani-Fard A A, Shirani G, "Classification and numbering of teeth in multi-slice CT images using wavelet-Fourier descriptor", Int J Comput Assist Radiol Surg., 2010 5 (3), p. 237-249; Miki Y, Muramatsu C, Hayashi T, Zhou X, Hara T, Katsumata A, et al., "Classification of teeth in cone-beam CT using deep convolutional neural network", Comput Biol Med. 2016 80, pp. 24-29.

Segmentation techniques may be implemented for more accurate localization. While the example above employed the CNN architecture, those skilled in the art will recognize the implementation of the above system and methodology need not be limited to CNNs and that other architectures and networks may be employed to further improve the accuracy of this example, especially for diagnostics of pathologies. It will also be appreciated by those skilled in the art that one advantage of the CNN approach is that these improvement steps can be gradual, and results of previous steps can be reused in the form of transfer learning: fine-tuning of existing models, training new models on already annotated datasets, segmentation or localization of objects within previously detected boundaries. It will also be appreciated that the system and methodology described herein can be employed to automate steps in diagnosis.

Implementation Example

The foregoing deep learning system can be implemented in a networked platform to provide computer-aided diagnostics and dental charting using radiographs or other dental images generated by one or more client systems to not only detect and number teeth, but also detect and identify conditions of individual teeth. Services provided by the networked system can include automatic completion of dental charts; automatic identification of areas of interest in dental images for professionals to investigate and potentially diagnose; and sharing of images, data and reports between dental practitioners and other parties, subject to applicable privacy constraints. These services may save time and reduce the negative effects associated with stress and fatigue in dental practice on the accurate analysis of dental imaging.

Figure 4:
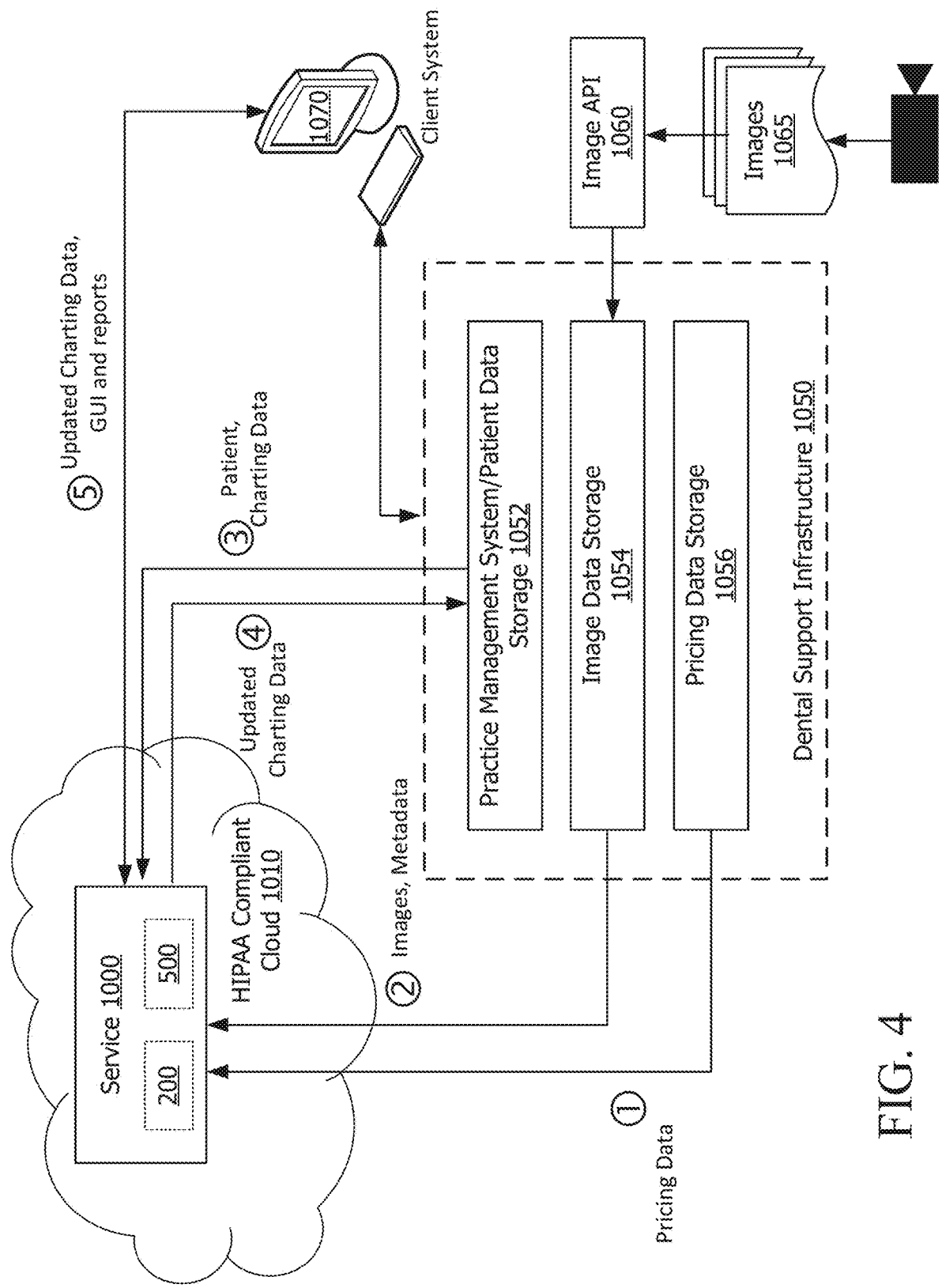
FIG. 4 is a schematic of a possible networked environment for the system of FIG. 1.

FIG. 4 illustrates an example network environment for the deep learning system. In this example, the detection and classification modules may be implemented in a cloud-based or networked analysis service 1000 communicating with one or more client systems. The cloud-based service 1000 is preferably operated in compliance with applicable privacy legislation, such as the United States Health Insurance Portability and Accountability Act of 1996 (HIPAA). Individual client systems 1070 may be computer systems in dental offices communicating with the cloud-based service 1000 via a wide area network. The client system 1070 communicates with the analysis service 1000 over a network to receive updated charting data and reports and to send responses (e.g., changes to provisional diagnoses), as described below. In one implementation, a web server (not shown) provides an interface between the analysis system 1000 and a browser client application executing on the client system 1070. Data supplied by the analysis system 1000 may be presented in graphical user interfaces as illustrated in FIGS. 5-9.

In a typical dental practice, it is expected that practitioners implement practice management software for the creation and management of patient data, including dental images. Individual dental practices may also establish their own price lists for services. This data (patient data, including dental images, and pricing data) may be stored locally in a client system 1070, or remotely by a practice management system 1052 and in image data storage 1054 and pricing data storage 1056 in a dental support infrastructure 1050. The dental support infrastructure 1050 may comprise a remote server system or cloud-based system, accessible by the client system 1070 via the Internet or other network. The infrastructure 1050 may be operated or hosted by a third party provider (e.g., a dental support organization); although in some implementations, the dental support infrastructure 1050, or one or more components of the infrastructure 1050 (e.g., the practice management system 1052) may be hosted locally in a dental office, e.g., co-located with the client system 1070. The infrastructure 1050 in turn may also communicate with the analysis service 1000 to provide the pricing data and image data to the analysis service 1000. The client system 1070 receives results generated by the analysis service 1000 through a web server of the analysis system 1000, as mentioned above, although alternatively the analysis service 1000 provides its results to the client system 1070 via the practice management system 1052.

As another example implementation, one or more components of the dental support infrastructure 1050 may be implemented in a cloud-based or networked system, integrated with the analysis system 1000. For example, the client system 1070 may access the dental support infrastructure components via a special-purpose computer program or web browser executing on the client system 1070. The special-purpose computer program or web browser communicates with a web server (not shown) that generates and transmits patient, analytical, and image data, including data generated by the analysis system 1000, to the client system 1070. Responses from the client system 1070 are sent to the dental support infrastructure 1050 and analysis system 1000 via the web server.

Communications between various components and elements of the network environment (analysis system 1000, dental support infrastructure 1050 and its components, the client system 1070) may occur over private or public connections, preferably with adequate security safeguards as are known in the art. In particular, if communications take place over a public network such as the Internet, suitable encryption is employed to safeguard the privacy of data exchanged between the various components of the network environment.

The service 200 implements the detection and classification modules 200, 500 described above, also preferably handling data in compliance with applicable privacy legislation. These various services and systems 1000, 1052, 1054, 1056, 1050 may be implemented by one or more servers, executing together in the same cloud-based environment; alternatively the practice management and data storage systems may reside on servers outside the cloud environment which communicate with the service 1000 over the same wide area network as the cloud environment, or over another network. The configuration of such servers and systems, including required processors and memory, operating systems, network communication subsystems, and the like, will be known to those skilled in the art.

In the example of FIG. 4, client systems 1070 interact with a remote practice management system 1052 for the management of patient data, pricing, and billing as well as viewing radiographic images. Images 1065 are collected at the client site using radiographic or other imaging equipment. The images are transferred to the image data storage 1054 over a network, for example using an application programming interface (API) 1060 to access the image data storage service. The images that are transmitted may be accompanied by metadata. It is expected that images will be generated in digital format and therefore ready for transmission over the network to the image data storage 1054; so, if radiographic images are generated on film, then as mentioned above, the images will be digitized first prior to transmission. The client system 1070 may subsequently retrieve the images 1065 from the image data storage 1054 for display locally. Optionally, pricing data may be provided by the client system 1070 to the pricing data storage 1056. The pricing data may then subsequently be transmitted (1) to the analysis service 1000 for use in generating responsive data, as discussed below. In addition, the collected image data and associated metadata (e.g., sufficient information to associate the image with a patient; numbering information (e.g., if the image is one of a series of images); the date of the image; the type of image (e.g., bitewing, PV, etc.); and information about the location of sensors or film, for example in the case of a bitewing radiograph) is transmitted (2) to the analysis service 1000. Additionally, patient data and charting data is transmitted for the patient (3). The charting data may comprise the patient's dental chart (in standard notation) from a previous visit or from the latest examinations if service 1000 is utilised for a quality assurance purpose.

The analysis service 1000 implements detection and numbering of present and absent teeth as described above, using the patient, charting, and image data received from the dental support infrastructure 1050. Using a similar methodology, the analysis service 1000 can also facilitate the detection and treatment of conditions: pathological conditions (e.g., missing teeth, caries, apical periodontitis, dental cysts), non-pathological conditions (e.g., restorations, crowns, implants, bridges, endodontic treatments) and post-treatment conditions (e.g., overhanging restorations, endodontic underfillings and overfillings). This automated detection of conditions may either replace or supplement detection and analysis of dental images by dental and medical practitioners. In addition to detecting and numbering teeth from input images, the analysis service 1000 is further trained and identifies and classifies regions of interest within detected teeth, to enable the generation of a symbolic dental chart with conditions provisionally identified or diagnosed for delivery through a computer interface to the practitioner, e.g., via the practitioner's practice management software. For example, the analysis service 1000 may enable rapid analysis of dental X-ray images, highlighting of teeth with radiological findings, providing supporting data, and present preliminary findings for confirmation or rejection by practitioners to generate final assessment reports. Detection of pathological conditions and radiological findings can be performed using, again, an appropriately trained CNN or other neural network architecture. Alternatively, conditions and findings may be diagnosed by a practitioner and input manually via a user input interface at a client system. The results generated by the analysis service 1000 are provided in the form of updated charting data (4) to the practice management system 1052 (as mentioned above, this may be in accordance with a preferred standard notation), optionally with preliminary diagnostic findings correlated to tooth numbers that were automatically determined by the service 1000. The updated charting data may also comprise an indication of the bounding box or region of interest for the input image as identified during either the tooth detection or condition detection by the analysis service 1000. This region of interest information may comprise coordinates defining each portion of the original image (e.g., coordinates identifying absolute pixel positions within the image, or coordinates and offsets defining a rectangular region within the image) for which a tooth and/or a condition was detected, associated with a corresponding tooth number. If a condition was determined from the region of interest identified by the coordinates, then the updated charting data also comprises an identifier of the condition associated with the tooth number and the coordinates.

In these examples, charting and patient data may be maintained in an electronic form and handled in conformance with privacy requirements and established standards such as ANSI/ADA 1067:2013, Electronic Dental Record System Standard Functional Requirements. Further, the data preferably conforms to one or more established standards or conventions including the aforementioned FDI and Universal numbering systems, and transaction and code set standards as may be defined for dental practice, such as codes on dental nomenclature and coding mandated by HIPAA or other equivalent legislation or regulation, or other standardized codes such as the Code on Dental Procedures and Nomenclature (CDT Code) published by the American Dental Association.

In one implementation, the updated charting data may be displayed in a graphical user interface (GUI) on a chair-side display of the client system 1070 to practitioners and/or patients to visualise diagnostic findings. This data and GUI may be served from the analysis system 1000 directly to the client system 1070 (5). After practitioners confirm, rule out or add new findings based on clinical examinations and their professional opinions, assessment reports with supporting data, including the ability to download an X-Ray or other image, and practitioner recommendations may be generated by the analysis system 1000 and transmitted (5) to the client system 1070 for sharing with patients electronically. It will be appreciated from the following examples that automatic detecting and numbering the teeth from radiographs and other types of input images by the analysis system 1000 permits the generation of symbolic dental chart with associated annotations correlating one or more specific conditions, as identified by the analysis system 1000 and the association of detected conditions to a tooth number.

Figure 5:
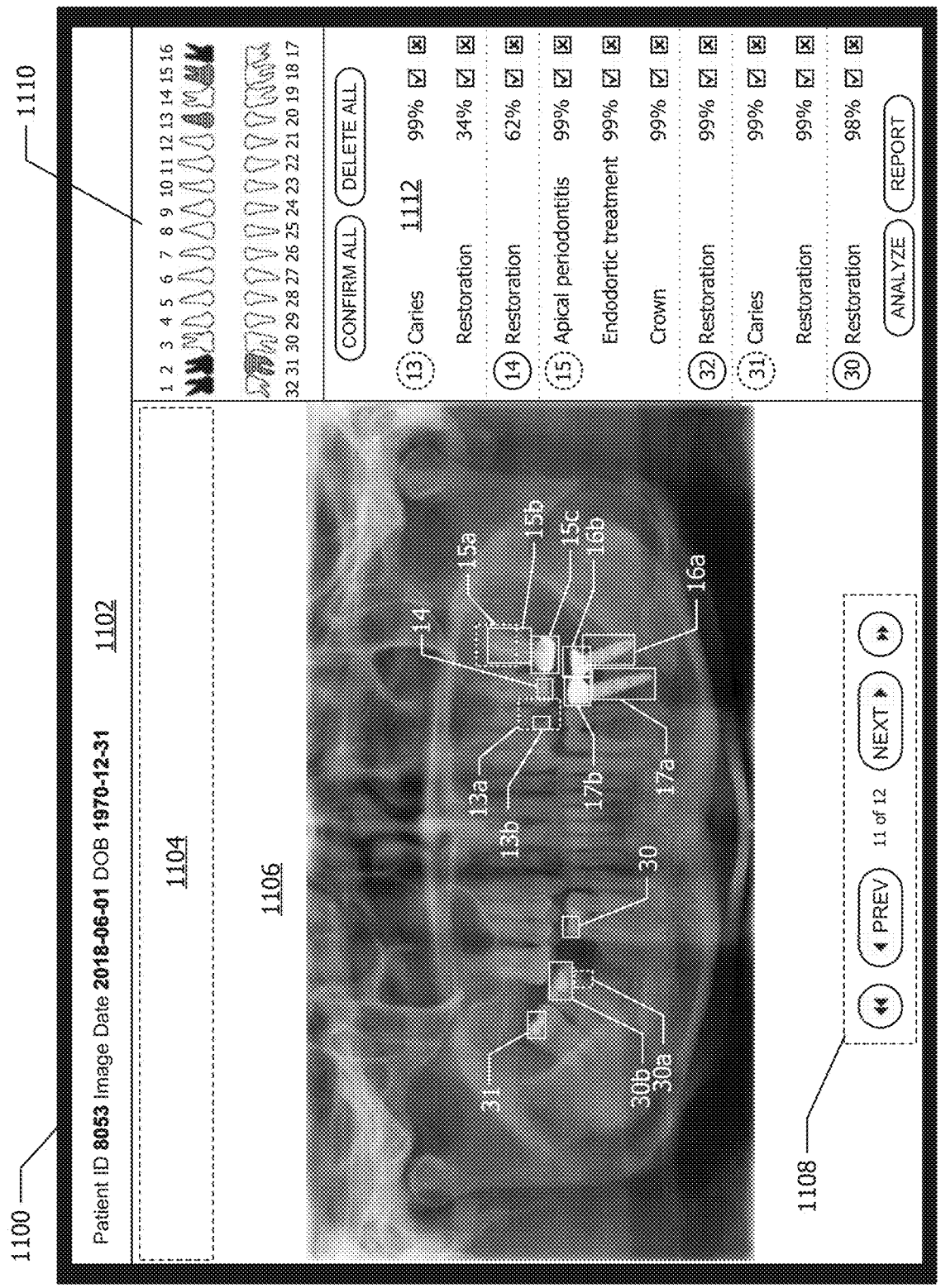
FIG. 5 is an illustration of an example graphical user interface on a client system displaying a panoramic radiograph based on the detection and classification executed by the system of FIG. 1.
Figure 6:
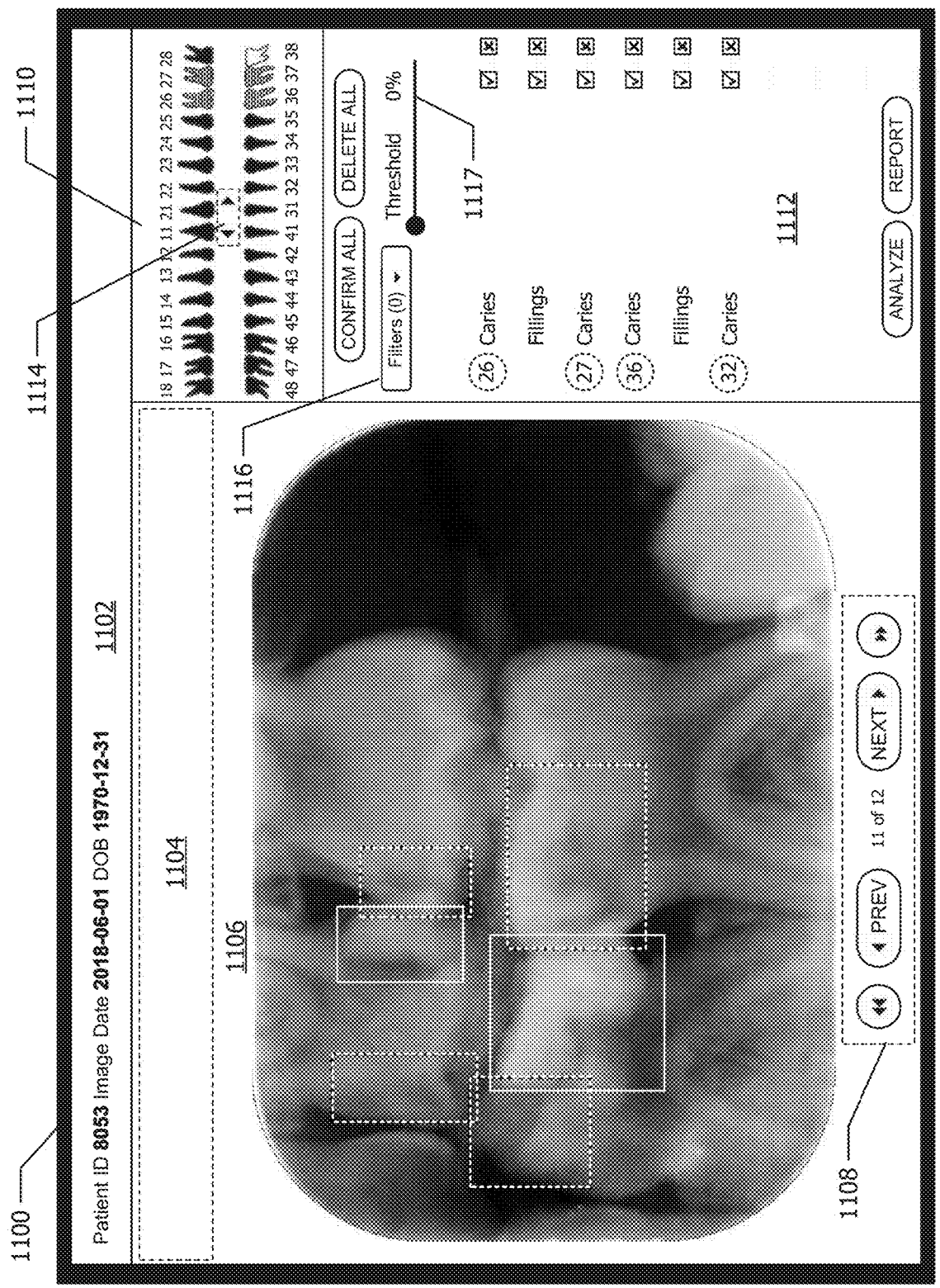
FIG. 6 is an illustration of a graphical user interface on a client system displaying a bitewing radiograph based on the detection and classification executed by the system of FIG. 1.
Figure 7:
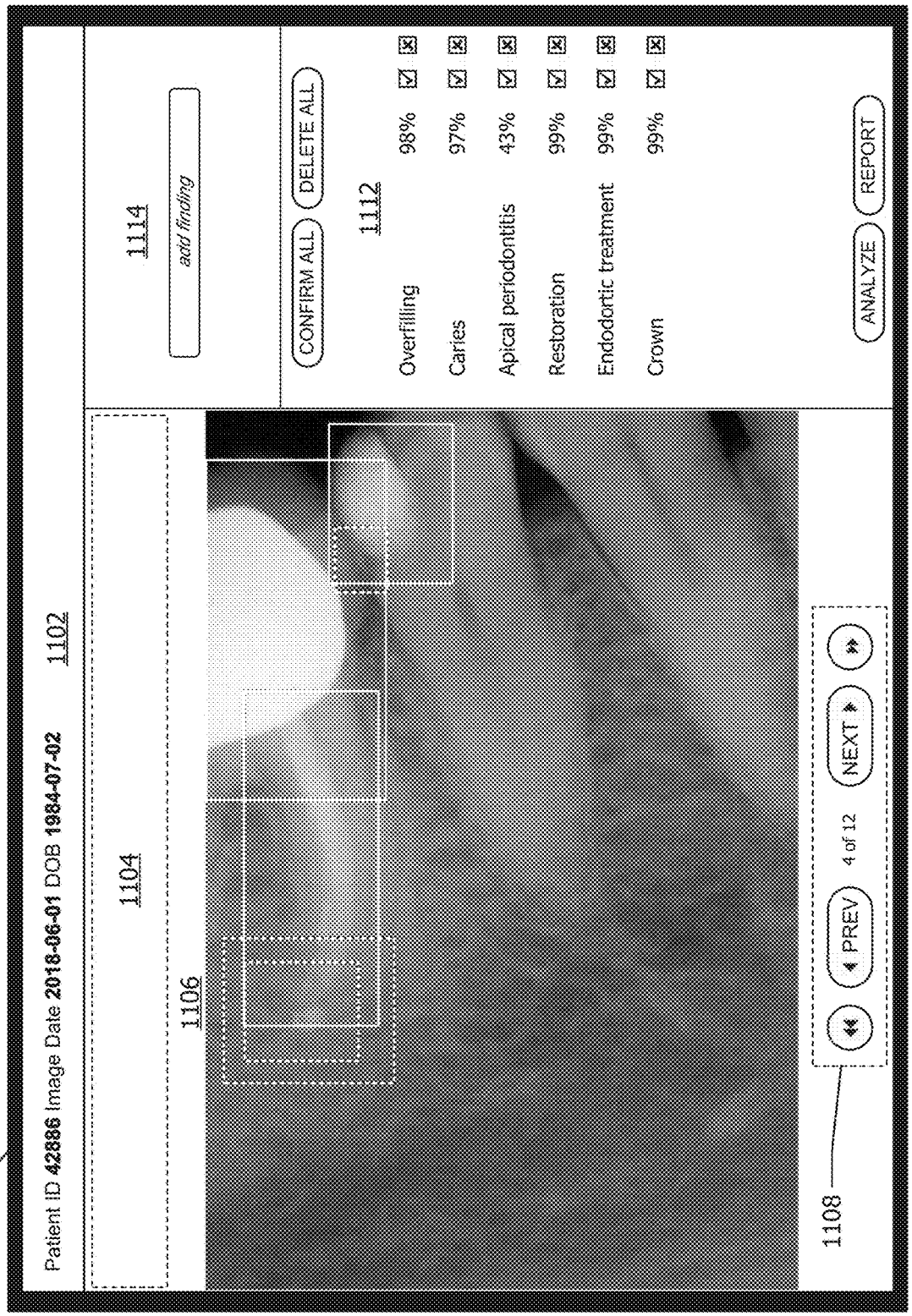
FIG. 7 is an illustration of a further example graphical user interface displaying an X-ray image based on output by the system of FIG. 1.

FIGS. 5 to 7 illustrate a number of example GUIs 1100 that may be displayed by a client program executing at the client system 1070. A preliminary assessment generated by the service 1000 may be transmitted to the client system 1070 and rendered in a GUI such as GUI 1100. In this example, the service 1000 not only performs the detection and classification (numbering) described above, but also detects and classifies non-pathological and pathological conditions from the images. The classification (numbering) and detected conditions are identified in the updated charting data transmitted to the practice management system 1052 (4). This information can be retrieved, along with the image data, by the client system 1070 and displayed in a GUI such as the GUI 1100. The first example GUI of FIG. 5 comprises a patient information display area 1102 (in the figures, hypothetical patient data is shown); image manipulation interface 1104 (illustrated schematically), which may include different user interface elements such as buttons, sliders, etc. for manipulating the dental image displayed in the image area 1106. For example, user interface elements may be provided for altering the brightness and contrast of the image; zooming in or out; panning in different directions; marking up the image; and so on. The GUI may also be provided with a menu bar (not illustrated in the figures) for carrying out various tasks such as saving altered images; sending reports or images to a recipient; loading new patient information; and so on. Since a series of images may have been generated for a given patient at a single consultation, the GUI can include navigation elements 1108 for navigating to other images in the series.

The example GUI of FIG. 5 also presents the detected non-pathological and pathological conditions for the patient in different forms. In addition to the patient's PV image displayed in image area 1106, the detected conditions can be indicated by bounding boxes or other visual elements on the displayed image. The locations and dimensions of the bounding boxes or visual elements may be determined by the regions of interest previously identified by the analysis service 1000, and can be visually distinguished according to the type of condition detected. For example, non-pathological conditions may be marked on the image in a first color, while pathological conditions are marked on the image using a different color. In the accompanying figures, non-pathological conditions are indicated with a solid line rectangle, while pathological conditions are indicated in a dashed line rectangle. The GUI 1100 may also include user interface elements to permit the user to show or hide visual elements of a certain type (e.g., to hide all the non-pathological visual elements).

Furthermore, a standard symbolic numbered dental chart 1110 is also displayed, comprising a plurality of teeth representing the typical arrangement of a full complement of adult teeth (or primary teeth as appropriate) mapped or correlated to tooth position, number (classification), and detected conditions. The dental chart may also be color coded to signal the location of non-pathological and pathological conditions. The color coding may match color coding used elsewhere in the GUI (e.g., in the image region 1106). In addition, teeth that appear in the standard chart that are not detected (e.g., because the patient lacks those teeth) may be shown greyed-out. In some implementations of the GUI, a user may select (e.g., using a pointing device or touch interface device, such as a touchscreen) a single tooth in the chart, and the detected conditions may be displayed adjacent to the tooth. Thus, at least some teeth depicted symbolically in the dental chart 1110 are correlated to the regions of interest identified by the bounding boxes or other visual elements in the displayed image in image area 1106.

In addition, a listing 1112 of the detected conditions is also included. in the example of FIG. 5, the list entries are correlated to a corresponding tooth by number and a confidence level for the detected condition (e.g. "13 Caries 99%" indicates that a cavity was detected in tooth number 13 with a confidence level of 99%). Teeth that are identified as present in the dental chart but otherwise exhibit no pathological or non-pathological conditions (i.e., "normal" teeth) may be omitted from the listing of the detected conditions, or may be included in the listing and indicated as being normal. The mapping or correlation to the chart 1110 may be carried out either by the service 1000 and transmitted as part of the GUI data to the client system 1070, or alternatively the mapping or correlation may be constructed by the client system 1070 on receipt of the listing data.

The listing may include user interface elements, such as checkboxes, for the practitioner to confirm or reject (delete) the findings made by the service 1000. Confirmations and rejections, if submitted by the practitioner, are sent to the service 1000 as feedback (again, this may be in the form of charting data (3)) and may be used to provide additional training to the CNN or other neural network.

FIG. 6 is a further example of the GUI 1100, displaying a bitewing radiograph in the image area 1106. In this case, as a bitewing image captures only a subset of a patient's teeth, not every tooth in the standard dental chart 1110 is visible in the image. Accordingly, the standard dental chart 1110 may grey-out those teeth that are not currently visible. Additional navigation elements 1114 may also be provided adjacent the standard dental chart 1110 to permit the user to switch to an image displaying adjacent teeth, assuming that a series of images for the patient is available. Since the analysis system 1000 is able to determine the number of teeth in the series of images, the next image in the series can be identified and retrieved.

In the example of FIG. 6, the listing 1112 includes options for the user to filter 1116 the displayed results (e.g., to display caries only, or all detected pathological conditions, etc.). Filtering may also be used to exclude detected conditions having an associated confidence level lower than a selected threshold. In this example, a slider 1117 is provided to permit the user to input a desired confidence level threshold.

Figure 8:
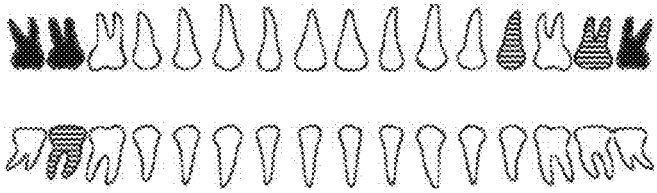
FIG. 8 is an illustration of an example report generated at the client system based on the output by the system of FIG. 1.
Figure 9:
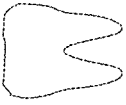
FIG. 9 is an illustration of an example portion of a graphical user interface or report generated using the output of the system of FIG. 1.

Since CNNs rely only on "raw" image data, and do not rely on hand-crafted features or special-purpose programming to be able to detect features in the dental images, the techniques described above extend to the interpretation of various other types of dental X-ray images such as periapical intraoral radiographs, full-mouth series, or 3D images such as cone beam computed tomographs, and may be extended to craniofacial X-ray images such as cephalograms, as well as intraoral and extraoral camera images, videos, and 3D scans. FIGS. 7, 8, and 9 illustrate further example GUIs 1100 containing the results of a periapical image analysis, a bitewing image analysis, and a filtered bitewing image analysis, respectively. FIG. 7 includes a listing of probable pathological, non-pathological and problematic post-treatment conditions; FIG. 8 lists probable pathological and non-pathological conditions, and the listing of FIG. 9 is filtered to show only probable pathological conditions.

Again, the listings may include corresponding confidence levels and provide an option for the practitioner to confirm or reject these findings.

As mentioned above, if the practitioner confirms or rejects findings, these responses may be transmitted to the analysis service 1000 for incorporation into training data for future analyses. In addition, the results displayed in the GUI 1100 are updated to remove any rejected entries. As shown in FIGS. 7 to 9, in place of the dental chart 1114 an option to input new findings is provided. These added findings (tooth number, diagnosis) can also be transmitted as new charting data (3) to the analysis service for incorporation into training data. The listing 112 is also correspondingly updated.

Once the practitioner has completed their review of the reported findings in the GUI, different forms of reports may be generated. As one example, an orthopantomogram report may be generated based on the diagnosis generated from a PV image. An example of a report 1120 is shown in FIG. 10. This report includes a finalized version of the standard dental chart 1122; a listing, by tooth number (American notation is employed in FIG. 19) of teeth that were determined to be present ("Normal appearance") and missing, together with a listing of the findings as confirmed by the practitioner 1124. In this report 1120, which is displayable by the client system 1070, fields are available for the practitioner to enter comments. The report 1120 also includes images cropped from the original PV image for each tooth having a corresponding finding 1126. The report 1120 thus presents the detected conditions (as confirmed or edited by the practitioner) in multiple formats.

Based on the detected pathological conditions the service 1000 can additionally generate treatment planning data and transmit this data to the practice management system 1052 for retrieval by the client system 1070. Treatment planning data may include, at a minimum, a tooth identification (e.g., number) for each tooth having a detected pathological condition and a prescribed treatment for the pathological condition (the correlation between the prescribed treatment and the pathological condition may be included in the configuration records). The treatment planning data can be updated and transmitted again in response to receipt by the system 1000 of changes to the diagnosed conditions as a result of the practitioner rejecting a diagnosis, or adding a new finding.

Furthermore, if pricing data is provided (1) to the analysis service 1000, based on the treatment planning data and patient data recorded by the client systems concerning treatments actually carried out, the analysis system 1000 can also track potential revenue from projected treatments (e.g., by aggregating the treatment planning data) and actual revenue from treatments.

Another possible report is a patient education document or GUI view, depicting the projected costs of treatment for a given tooth depending on the time of treatment. An example interface 1200 is depicted in FIG. 9, for a scenario in which a caries is detected in a tooth. An initial projected cost for treating the caries immediately with a filling may be $100 (as an example). However, if the patient chooses not to treat the condition immediately, in 1-2 years, both a filling and onlay may be required, with an estimated cost of $3000. In 2-3 years, a filling, root canal, and crown may be required, for a cost of $1600. If the condition is left untreated for 3 years or more, extraction may be required, resulting in the need for an implant and crown, for a total estimated cost of $3950. Based on the identification and detection of tooth conditions by the analysis system 1000, the analysis system 1000 can identify a corresponding treatment and retrieve the pricing data from the pricing data storage 1056 to compute a provisional cost of treatment. Further, the analysis system 1000 can compute a projected diagnosis for the tooth if left untreated based on the tooth numbering and the condition of adjacent teeth, and retrieve costs associated with treatment at specified time intervals to provide a projected cost of treatment at later dates. This information can be transmitted to the client system 1070 and displayed together with standardized graphics representing the process of the pathological condition over time to effectively educate the patient on the options for treatment, and the consequences of non-treatment, as depicted in 1200.

These systems and methods may further enable batch analysis of dental imaging to, for example, a) compare the information in existing dental charts and dental records with the content of a practice's patients' dental images, and b) identify post-treatment conditions in post-treatment images. For example, a practice or a dental plan provider may review all or a subset of its patient files to identify incomplete dental charts, probable missed pathological findings or incorrectly detected, as well as treatment plans that are not in accordance to the standard of care, as part of its pre-treatment quality assurance process. Also, a practice or a dental plan provider may review all or a subset of its patient files to identify problematic or exemplary procedures as part of its post-treatment quality assurance process. The images may be sorted by the probability of discrepancies or problematic post-treatment findings and presented to a qualified professional for further analysis, as shown in the example GUIs or in the form of data supplied to third-party analytics and business intelligence systems.

In still another aspect, these systems and methods may enable the provision of objective assessments to support practitioner findings. This may engender greater patient trust in practitioner decision-making, and may educate and encourage patients to obtain treatment for diagnosed conditions.

The examples and embodiments are presented only by way of example and are not meant to limit the scope of the subject matter described herein. Variations of these examples and embodiments will be apparent to those in the art and are considered to be within the scope of the subject matter described herein. For example, some steps or acts in a process or method may be reordered or omitted, and features and aspects described in respect of one embodiment may be incorporated into other described embodiments.

The data employed by the systems, devices, and methods described herein may be stored in one or more data stores. The data stores can be of many different types of storage devices and programming constructs, such as RAM, ROM, flash memory, programming data structures, programming variables, and so forth. Code adapted to provide the systems and methods described above may be provided on many different types of computer-readable media including computer storage mechanisms (e.g., CD-ROM, diskette, RAM, flash memory, computer's hard drive, etc.) that contain instructions for use in execution by one or more processors to perform the operations described herein. The media on which the code may be provided is generally considered to be non-transitory or physical.

Computer components, software modules, engines, functions, and data structures may be connected directly or indirectly to each other in order to allow the flow of data needed for their operations. Various functional units have been expressly or implicitly described as modules, engines, or similar terminology, in order to more particularly emphasize their independent implementation and operation. Such units may be implemented in a unit of code, a subroutine unit, object (as in an object-oriented paradigm), applet, script or other form of code. Such functional units may also be implemented in hardware circuits comprising custom VLSI circuits or gate arrays; field-programmable gate arrays; programmable array logic; programmable logic devices; commercially available logic chips, transistors, and other such components. Functional units need not be physically located together, but may reside in different locations, such as over several electronic devices or memory devices, capable of being logically joined for execution. Functional units may also be implemented as combinations of software and hardware, such as a processor operating on a set of operational data or instructions.

It should also be understood that steps and the order of the steps in the processes and methods described herein may be altered, modified and/or augmented and still achieve the desired outcome. Throughout the specification, terms such as "may" and "can" are used interchangeably. Use of any particular term should not be construed as limiting the scope or requiring experimentation to implement the claimed subject matter or embodiments described herein. Any suggestion of substitutability of the data processing systems or environments for other implementation means should not be construed as an admission that the invention(s) described herein are abstract, or that the data processing systems or their components are non-essential to the invention(s) described herein. Further, while this disclosure may have articulated specific technical problems that are addressed by the invention(s), the disclosure is not intended to be limiting in this regard; the person of ordinary skill in the art will readily recognize other technical problems addressed by the invention(s).

The invention claimed is:

1. A computer-implemented method, comprising:
    obtaining a two-dimensional (2D) dental image comprising one or more teeth, the 2D dental image comprising:
    an X-ray image depicting a pair of overlapping teeth, an impacted tooth, or a tooth with a crown;
    obtaining a tooth number for one or more teeth comprised in the 2D dental image, wherein the obtaining comprises:
        using a computer system executing a plurality of trained neural network models, identifying the one or more teeth in the 2D dental image and determining a tooth number associated with the identified one or more teeth,
        wherein determining the tooth number comprises determining the tooth number for the pair of overlapping teeth, the impacted tooth, or the tooth with a crown; and
    transmitting, to a system, data associated with the identified one or more teeth comprising the corresponding tooth number.

2. The computer-implemented method of claim 1, wherein transmitting the data comprises transmitting the data to a practice management system, to a business intelligence system, to a review system used by a dental plan provider, or for storage in an electronic health record.

3. The computer-implemented method of claim 1, further comprising:
    obtaining a diagnosis of at least one condition for at least one of the identified one or more teeth comprised in the 2D dental image, and wherein the transmitted data comprises an identification of the at least one condition associated with the corresponding tooth number of the at least one of the identified one or more teeth.

4. The computer-implemented method of claim 3, wherein the at least one condition comprises at least one of a pathological condition, a non-pathological condition, or a post-treatment condition, and wherein:
    the pathological condition comprises one of a missing tooth, caries, apical periodontitis, or cyst;
    the non-pathological conditions comprises one of a restoration, crown, implant, bridge, or endodontic treatment; and
    the post-treatment condition comprises one of an overhanging restoration, endodontic underfilling, or overfilling.

5. The computer-implemented method of claim 3, wherein the transmitted data further comprises the 2D dental image with a visual indication of a corresponding location of the at least one condition in the 2D dental image for display at a recipient computer system.

6. The computer-implemented method of claim 1, wherein the transmitted data further comprises data correlating a location in the 2D dental image of the identified one or more teeth with a corresponding tooth in a symbolic dental chart for display at a recipient computer system.

7. A computer-implemented system, comprising:
    a network communication subsystem, and at least one processor configured to:
        obtain a two-dimensional (2D) dental image comprising one or more teeth, the 2D dental image comprising:
        an X-ray image depicting a pair of overlapping teeth, an impacted tooth, or a tooth with a crown;
        obtain a tooth number for one or more teeth comprised in the 2D dental image, wherein the obtaining comprises a plurality of trained neural network models identifying the one or more teeth in the 2D dental image and determining a tooth number associated with the identified one or more teeth,
        wherein determining the tooth number comprises determining the tooth number for the pair of overlapping teeth, the impacted tooth, or the tooth with a crown; and
        transmit data associated with the identified one or more teeth comprising the corresponding tooth number.

8. The computer-implemented system of claim 7, wherein transmitting the data comprises transmitting the data to a practice management system, to a business intelligence system, to a review system used by a dental plan provider, or for storage in an electronic health record.

9. The computer-implemented system of claim 7, wherein the at least one processor is further configured to:
    obtain a diagnosis of at least one condition for at least one of the identified one or more teeth comprised in the 2D dental image, and
    wherein the transmitted data comprises an identification of the at least one condition associated with the corresponding tooth number of the at least one of the identified one or more teeth.

10. The computer-implemented system of claim 9, wherein the at least one condition comprises at least one of a pathological condition, a non-pathological condition, or a post-treatment condition, and wherein:
    the pathological condition comprises one of a missing tooth, caries, apical periodontitis, or cyst;
    the non-pathological conditions comprises one of a restoration, crown, implant, bridge, or endodontic treatment; and the post-treatment condition comprises one of an overhanging restoration, endodontic underfilling, or overfilling.

11. The computer-implemented system of claim 9, wherein the transmitted data further comprises the 2D dental image with a visual indication of a corresponding location of the at least one condition in the 2D dental image for display at a recipient computer system.

12. The computer-implemented system of claim 7, wherein the transmitted data further comprises data correlating a location in the 2D dental image of the identified one or more teeth with a corresponding tooth in a symbolic dental chart for display at a recipient computer system.

13. The computer-implemented method of claim 3, wherein the transmitted data further comprises at least one standardized code associated with the at least one condition.

14. The computer-implemented method of claim 3, wherein the at least one condition is pathological, and the transmitted data further comprises treatment planning data for each detected tooth associated with the at least one condition.

15. The computer-implemented method of claim 3, wherein the at least one condition is pathological, and the transmitted data further comprises patient education information relating to treatment of the at least one condition.

16. The computer-implemented method of claim 1, wherein the plurality of trained neural network models comprises trained neural networks executing a detection task and a classification task.

17. The computer-implemented method of claim 16, wherein the detection task comprises detecting the one or more teeth in the 2D dental image and providing image data obtained from the 2D dental image corresponding to the one or more teeth as an output; and
the classification task comprises determining a tooth number associated with each of the one or more teeth based on the output of the detection module.

18. The computer-implemented method of claim 1, wherein the plurality of trained neural network models comprises trained neural networks executing a segmentation task and a classification task.

19. The computer-implemented method of claim 18, wherein the segmentation task comprises segmenting the one or more teeth in the 2D dental image and providing image data from the 2D dental image corresponding to the one or more teeth as an output; and
the classification task comprises determining a tooth number associated with each of the one or more teeth based on the output of the detection module.

20. The computer-implemented method of claim 3, wherein obtaining the diagnosis of the at least one condition comprises executing a classification module comprising a further trained neural network model on the detected one or more teeth.

21. The computer-implemented method of claim 1, wherein the 2D dental image comprises a panoramic view radiograph.

22. The computer-implemented method of claim 1, wherein the 2D dental image comprises an intraoral radiograph.

23. The computer-implemented system of claim 9, wherein the transmitted data further comprises at least one standardized code associated with the at least one condition.

24. The computer-implemented system of claim 9, wherein the at least one condition is pathological, and the transmitted data further comprises treatment planning data for each detected tooth associated with the at least one condition.

25. The computer-implemented system of claim 9, wherein the at least one condition is pathological, and the transmitted data further comprises patient education information relating to treatment of the at least one condition.

26. The computer-implemented system of claim 7, wherein the plurality of trained neural network models comprises trained neural networks executing a detection task and a classification task.

27. The computer-implemented system of claim 26, wherein the detection task comprises detecting the one or more teeth in the 2D dental image and providing image data obtained from the 2D dental image corresponding to the one or more teeth as an output; and
the classification task comprises determining a tooth number associated with each of the one or more teeth based on the output of the detection module.

28. The computer-implemented system of claim 7, wherein the plurality of trained neural network models comprises trained neural networks executing a segmentation task and a classification task.

29. The computer-implemented system of claim 28, wherein the segmentation task comprises segmenting the one or more teeth in the 2D dental image and providing image data obtained from the 2D dental image corresponding to the one or more teeth as an output; and
the classification task comprises determining a tooth number associated with each of the one or more teeth based on the output of the detection module.

30. The computer-implemented system of claim 9, wherein obtaining the diagnosis of the at least one condition comprises executing a classification module comprising a further trained neural network model on the detected one or more teeth.

31. The computer-implemented system of claim 7, wherein the 2D dental image comprises a panoramic view radiograph.

32. The computer-implemented system of claim 7, wherein the 2D dental image comprises an intraoral radiograph.

* * * * *